United States Patent [19]

Patko

[11] Patent Number: 5,098,545

[45] Date of Patent: Mar. 24, 1992

[54] PRECALIBRATED, DISPOSABLE ELECTROCHEMICAL SENSING DEVICE

[76] Inventor: Martin J. Patko, 11 Aberdeen, Irvine, Calif. 92720

[21] Appl. No.: 626,411

[22] Filed: Dec. 14, 1990

Related U.S. Application Data

[63] Continuation of Ser. No. 401,786, Sep. 1, 1989, abandoned, which is a continuation of Ser. No. 220,246, abandoned.

[51] Int. Cl.$^5$ ............................................ G01N 27/26
[52] U.S. Cl. ...................................... 204/403; 204/414; 204/415; 204/416; 204/433; 204/412
[58] Field of Search ............... 204/1 T, 195 R, 195 P, 204/416, 414, 415, 416, 403, 412, 433

[56] References Cited

U.S. PATENT DOCUMENTS

| | | | |
|---|---|---|---|
| 3,357,908 | 12/1967 | Riseman et al. | 204/415 |
| 3,707,455 | 12/1972 | Derr et al. | 204/403 |
| 4,225,410 | 9/1980 | Pace | 204/412 |
| 4,452,682 | 6/1984 | Takata et al. | 204/403 |
| 4,654,127 | 3/1987 | Baker et al. | 204/1 T |
| 4,713,165 | 12/1987 | Conover et al. | 204/403 |

OTHER PUBLICATIONS

T. S. Ma et al., "Organic Analysis Using Ion-Selective Electrodes", vol. I Methods, pp. 62–136, (1982).

*Primary Examiner*—John Niebling
*Assistant Examiner*—Bruce F. Bell
*Attorney, Agent, or Firm*—Herb Boswell

[57] ABSTRACT

Precalibrated, disposable electrochemical sensing devices can be constructed so as to utilize a housing shaped so as to internally include at least two separate half cells, one of which is capable of serving as a reference half cell and the other of which is capable of serving as a sensing half cell. The housing is shaped so as to include a top depression capable of being used as a container which is in communication with the interiors of the half cells. The depression is capable of holding for a sample to be analyzed using the device. The housing is preferably mounted on a board which is capable of being plugged into a female socket. This board carries electrodes which are connected to electrodes in the half cells.

10 Claims, 3 Drawing Sheets

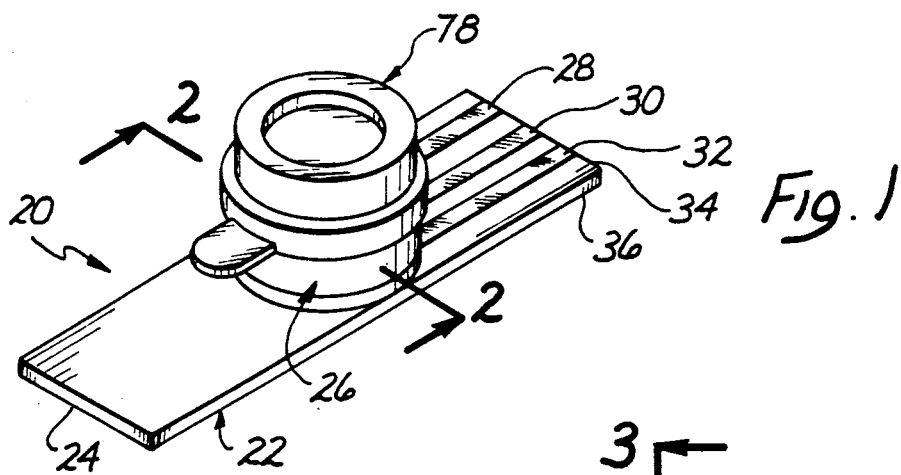
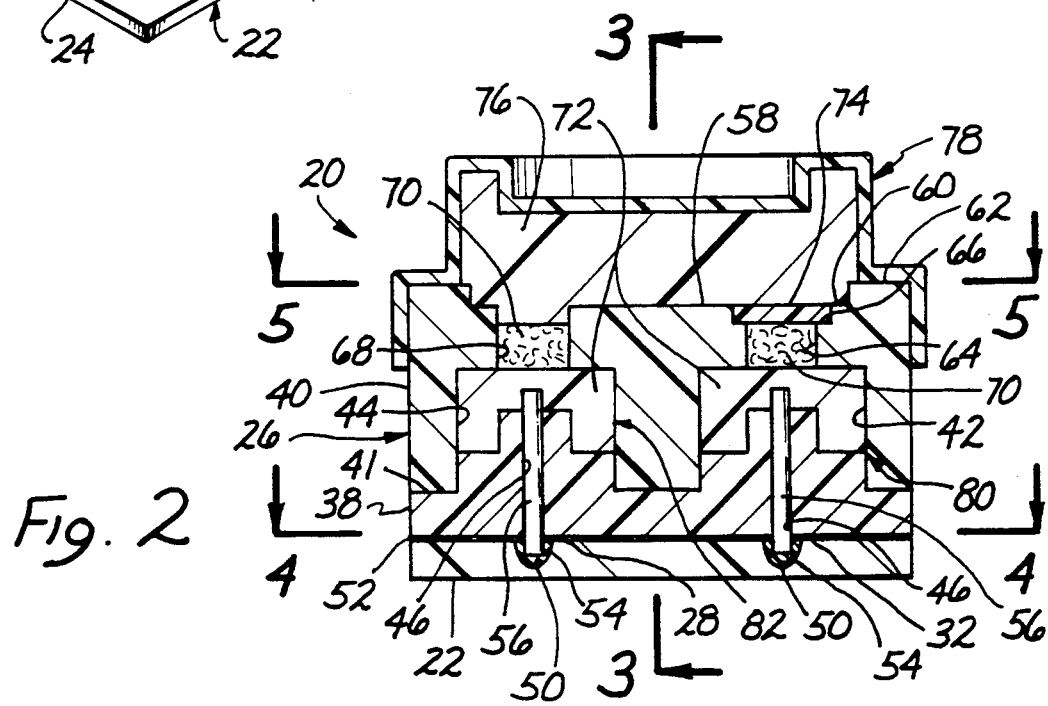
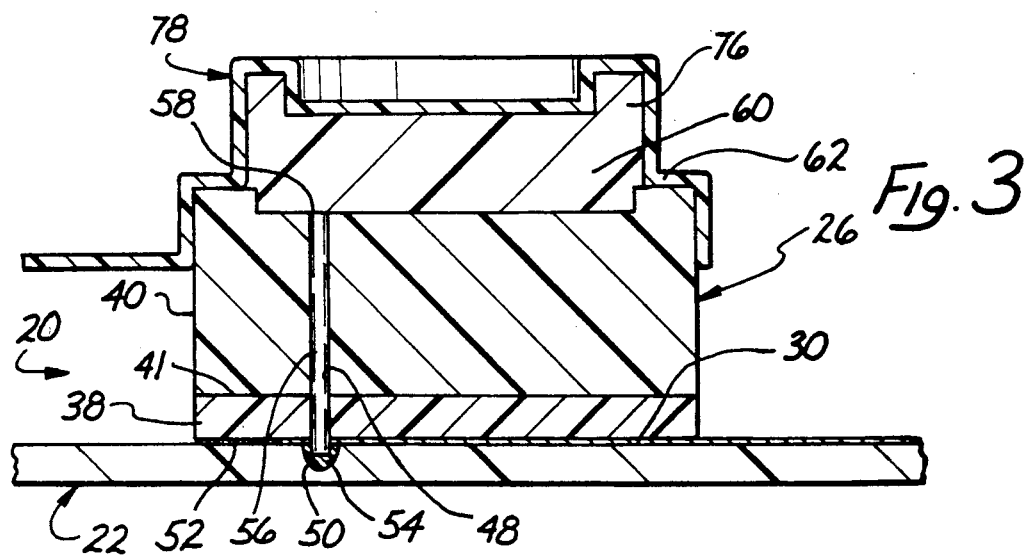

PRECALIBRATED, DISPOSABLE ELECTROCHEMICAL SENSING DEVICE

CROSS-REFERENCE TO RELATED APPLICATION

This application is a continuation of application Ser. No. 07/401,786, filed Sep. 1, 1989, now abandoned, which is a continuation of the copending U.S. patent application by the inventor named herein entitled "Precalibrated, Disposable, Electrochemical Sensors", Ser. No. 07/220,246, filed July 10, 1988.

BACKGROUND OF THE INVENTION

The invention set forth in this specification pertains to new and improved disposable, electrochemical sensing devices. More specifically it pertains to sensing devices or sensors which are used in conjunction with appropriate electronic apparatus in order to determine the content of certain specific ions or gases in various different fluids.

In many different medical, ecological and industrial circumstances it is necessary or desirable to determine whether or not a specific ion, ions of a group of closely related ions, a gas or gases of a group of gases of a closely related character are or are not present within a fluid and, if such an ion, gas or group of either is present, the amount of the latter which is present in the fluid. Thus, for example, in the medical field it is often necessary to determine the potassium, oxygen or other content of blood. Similarly, in monitoring various industrial processes it is frequently necessary to determine if a specific ion or gas is present in a solution or in a specific atmosphere such as ambient air, and, if it is, the quantity of the same which is present. Such determinations are needed and used in so many different areas of technology that it would be extremely time consuming to attempt to even suggest them all in this document.

Although determinations as are indicated in the preceding paragraph can be made in different manners in many cases whenever it is reasonably possible it is highly preferable to make such determinations electrochemicaly using ion or gas selective electrodes. The reasons for this are considered to be primarily related to the ease with which electrochemical measurements can be made, the comparatively low costs involved in making such measurements, the relative reliability of electrochemical analysis, and the fact that normally only comparatively limited equipment is required in order to make measurements to determine if an ion, a gas or a group of related ions or gases is present in a fluid, and, if so, the quantity of the latter present in the fluid.

Such equipment is closely related to that used in electrochemically making common pH measurements. It normally consists of a device having two separate electrochemical half cells, means for connecting the half cells by a sample of the fluid which is to be analyzed with the device and of an item of electronic equipment for making measurements in connection with the half cells and for indicating the results of such measurements. Although the physical structures of the cells used in a specific apparatus usually vary normally both cells used include a housing having an internal cavity, an electrode extending into the cavity and an electrolyte in the cavity in communication with the electrode. A half cell as described normally includes a flow control means such as a barrier, membrane or other structure for restricting flow between the electrolyte in the half cell and the means connecting it with the other half cell with which it is used.

The flow control means in one of the half cells is always of such a character as to permit essentially only movement of the ion or ions to be measured in or through such means or to permit a specific reaction or reactions with or absorption of the gas or gases to be measured in or at the surface of such means. Such a half cell is commonly referred to as a "sensing" cell or half cell. In a device employing two half cells as described the other or non-sensing half cell used normally employs a different flow control means than the sensing half cell. This latter half cell is utilized to provide a reference measurement for use in analyzing a corresponding measurement obtained using the sensing cell. Because of this the second cell in a device as described may be referred to as a "reference" cell or half cell.

As a result of its function the flow control means used as a part of the sensing half cell is quite critical to electrochemical sensing devices of the type to which this invention pertains. Ion or gas determinations using an electrochemical sensing device as indicated in the preceding discussion can be made only when an appropriate flow control device having a character as indicated in the preceding paragraph is available. As a consequence of this the flow control structure in a sensing half cell is restricted to an available membrane or barrier which is desirable in making a desired analysis. Fortunately advances in technology have resulted in and are resulting in membranes and barriers which are useful for an apparently ever increasing series of electrochemical determinations or measurements.

For some measurements it is considered necessary or preferable to use solid state membranes or barriers. The latter have been bodies of single crystals; they have also been bodies formed of particles such as small crystalline or other particles by such techniques as pressing such particles into a single, unitary mass. In some cases such particles have been physically held together with and/or within an inert or essentially inert binder. These membranes or barriers have also been prepared by forming polymer gels including one or more polymers and a fluid having desired ion selective or gas reactive or absorptive properties. It is common for the electrolyte in such half cell to contain the same ion or ions which are present in the membrane or barrier.

Fortunately an understanding of the invention does not require a detailed consideration of all of the different membranes or barriers capable of being used in devices in accordance with the invention. Neither does it require a detailed consideration of all of the diverse constructional details of known sensing and reference half cells of cells and of the various electrolytes employed in such cells in making determinations such as can be made using the devices of the present invention. However, an understanding of the reasons as to why the present invention is needed does require a brief, further discussion of prior devices which are related to the devices of the present invention.

Such prior devices are not considered to be completely satisfactory in meeting present and contemplated future needs for electrochemical sensing devices or sensors for one or more of a series of different reasons. Because of the diversity of such prior devices it is impractical to attempt to indicate all of the limitations and disadvantages of them in this document. Frequently such prior devices or sensors have been relatively complex and as a result of this undesirably expensive. Often such prior devices are comparatively difficult to use.

BRIEF SUMMARY OF THE INVENTION

As a result of the various limitations and disadvantages of prior sensing devices it is considered that that there is a need for new and improved sensing devices. Broadly the invention described in this document is intended to provide sensing devices which, to at least a significant extent, are more desirable in one or more ways than prior electrochemical sensing devices or sensors and which as a result of this tend to fulfill this need.

A more specific objective of the invention is to provide sensors as indicated which are desirable as compared to prior related sensors because of the fact that they can be supplied to a user in a precalibrated condition. This avoids the need for users of such sensors to calibrate them prior to their being used. The invention is also intended to provide electrochemical sensors which are normally sufficiently inexpensive so that they can be thrown away after they are used. This is important in that it avoids the expense of cleaning a sensor and avoids the possibility that a sensor may be contaminated when used after its initial use as a consequence of being inadequately cleaned.

A further objective of the invention is to provide electrochemical sensors as described which are specifically constructed so that they can be plugged into an appropriate electric type receptacle when they are used and which are of such a character that it is unnecessary to manipulate these sensors in any way after they are ready to be used. Another objective of the invention is to provide sensors which can be used to achieve relatively accurate measurements because of the presence of a grounding electrode within such sensors.

The invention is also intended to provide sensing devices of the type previously indicated which are constructed in such a manner that they can be easily and conveniently manufactured at a comparatively nominal cost and which are of such a character that they be easily and conveniently used with a comparative minimum of difficulty. Both the latter and the former are quite important from both a commercial and a practical standpoint. As normally supplied a sensor of the invention includes a cavity serving as a receptacle which is covered by an easily removable cover. The only operations required to use such a sensor in addition to plugging it in are to expose the interior of the cavity by a simple operation and then to insert a specimen or sample into the cavity. This is considered to contribute to the economics of the use of a sensing device of the invention.

These sensing devices are considered to be significant in that they can be constructed as subsequently described so as to be capable of either being used to perform a single determination or analysis from or on a specimen or sample or so as to be capable of being used to perform a series of separate analysis of determinations using such a single specimen. Although in many applications such as, for example, when only the potassium content of blood is of interest, there is no need for multiple analysis on other occasions it is considered that it will be quite important to substantially concurrently perform multiple determinations using only a single sample.

The preceding and other related objectives of the invention which will be apparent from a consideration of the remainder of this document are achieved by providing a device or unit for use in making electrochemical measurements which has two half cell means, each of said half cell means including a housing means, electrode means exposed to the interior of the cavity and extending to the exterior of the half cell means, electrolyte means located within said cavity in contact with said electrode means and membrane means enclosing said entrance and being in contact with said electrolyte means, said membrane means of one of said half cells being different from said membrane means of the other of said half cells and said membrane means of both of said half cell means being of such a character that said one of said half cell means can be used as a sensing cell and said other of said half cell means can be used as a reference cell in making electrochemical measurements and bridge means in communication with said entrances to said half cell means in which the improvement comprises at least one of the following:

(1) a body of an electrolyte means located within said bridge means and covering both of said membrane means, said body being capable of being removed from said bridge means so that it can be replaced by a sample to be analyzed; and (2) said bridge means being shaped as a receptacle having an open top and positioned so that a sample can be placed in or removed from said bridge means from the exterior of the unit and being a part of said housing means.

From a detailed consideration of the remainder of this document it is considered that it will be obvious that the invention includes many features and details which are important to the concepts of the invention and which are not specifically indicated in the preceding. As an example of this the body of the electrolyte means referred to in the preceding and the electrolyte means in said half cell means are preferably of the same electrochemical characteristics and this body is preferably easily removable from the bridge means so that it can be easily replaced by a sample or specimen. Also the open top of the bridge means is preferably covered prior to use by an easily removable cover to prevent contamination prior to the sensing device indicated being used.

BRIEF DESCRIPTION OF THE DRAWINGS

Because of the nature of the invention it is considered impractical to attempt to set forth all details of it in attempting to summarize it in the preceding. It is believed that the invention is best more fully explained with reference to the accompanying drawings in which:

FIG. 1 is an isometric view of a presently preferred embodiment or form of a sensing device or sensor of this invention for use in making a single analysis at a time with a cover in place on the device and with a removable body of an electrolyte in place within the device;

FIG. 2 is a partial side elevational view of the device shown in FIG. 1 at an enlarged scale;

FIG. 3 is a cross-sectional view of this device shown in FIG. 1 taken at line 3—3 of FIG. 2;

Figure 4:
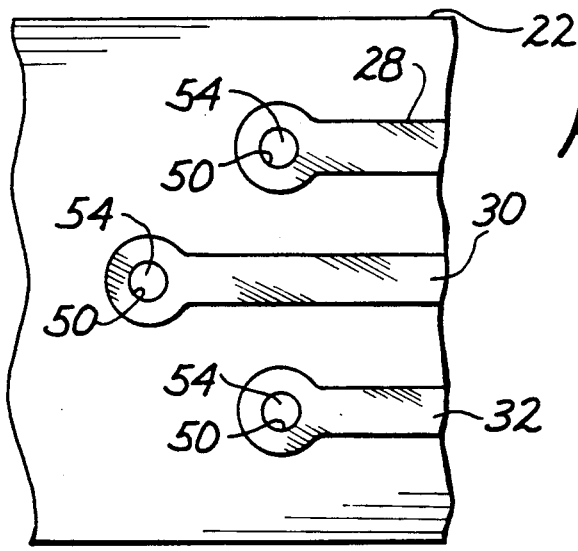
FIG. 4 is a partial cross-sectional view taken at line 4—4 of FIG. 2 showing the top side of the bottom board part of the device.
Figure 5:
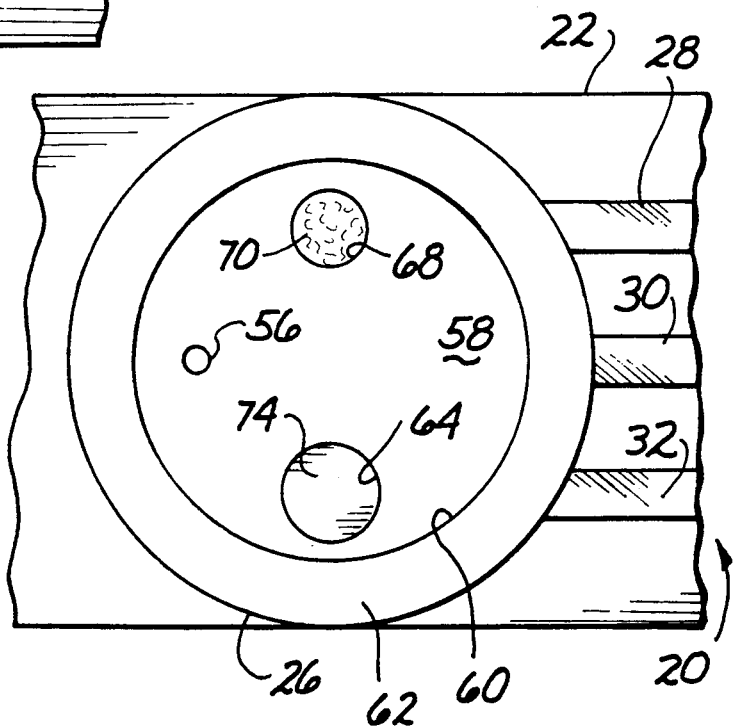
FIG. 5 is a partial top elevational view of the device shown in FIG. 1 with the cover for this device and an electrolyte body supplied to a user as a part of the device removed, this view corresponding to a partial cross-sectional view taken at line 5—5 of FIG. 2.

The two different embodiments or forms of sensing devices in accordance with the invention illustrated in the drawings are constructed so as to utilize the essentially intangible concepts or principles of the invention set forth and claimed in the appended claims. Those skilled in the field of designing equipment for use in making electrochemical determinations or analyses will realize that these concepts or principles can be used in other somewhat differently constructed and/or differently appearing devices or sensors through the use or exercise of routine skill in this field. For this reason the invention is not to be considered as being limited by the accompanying drawings.

DETAILED DESCRIPTION OF THE PREFERRED EMBODIMENTS

In the drawing there is shown a precalibrated, disposable electrochemical sensing device or sensor 20 in accordance with the invention as this device is normally supplied to a customer. This device 20 is constructed so as to include an elongated, substantially flat, electrically non-conductive bottom "board" or plate 22 which serves several functions. Normally this board 22 may be either a common printed circuit board or a separate part formed by common injection molding techniques. It has a tab or tab-like end portion 24 which is intended to be used in manipulating the device 20 as this device 20 is used. It also serves to support a housing 26 which, together with the various parts located in and on it as subsequently described, forms the primary functional "unit" (not separately numbered) of the entire device 20.

The board 22 also serves to support three separate strips 28, 30 and 32 of an electrical conductive material which extend along one another from an end 34 of the board 34 remote from the tab 24 to beneath the housing 26 where these strips 28, 30 and 32 are connected as subsequently described. The strips 28, 30 and 32 can be formed as any other conductors on a printed circuit board or can be formed out of a conventional electrically conductive adhesive polymer composition. Preferably they are sufficiently abrasion resistant so that they can be used as prongs on a common electrical plug to connect the entire device 20 to an appropriate electronic device (not shown) used with the device 20 to make measurements, determinations or analyses using the device 20.

Since the present invention is not concerned with such an electronic device and since suitable electronic apparatus for use with the device 20 is known no effort is made to describe such an appropriate electronic device in this document. Although the strips 28, 30 and 32 can be connected to such an electronic device using conventional means (not shown) such as common wires and spring biased conductive clips it is preferred to make the board 22 sufficiently stiff so that a user by holding the tab 24 can insert a portion 36 of the board 22 located between the housing 26 and the end 34 into an appropriate, conventional female socket (not shown) on such an electronic device. As a result of this the portion 36 of the board 22 can be referred to as a connector or male connector.

The housing 26 in the device 20 appears essentially as a small, short cylinder. As manufactured it is formed of two separate electrically non-conductive parts—a base 38 and a top 40—which are shaped as subsequently described. These parts 38 and 40 can be easily formed out of common polymers by conventional injection molding techniques. As formed they have adjacent surfaces 41 which are normally secured together by any convenient means such as ultrasonic welding or the use or an inert adhesive (not shown). These parts 38 and 40 are shaped so that as they are secured together along the surfaces 40 they define within the housing 26 two separate internal cavities 42 and 44.

The base 38 is shaped so as to include an elongated, vertically extending passage 46 extending into each of these cavities 42 and 44. Both the base 38 and the top 40 are shaped so as to include a third elongated, vertically extending passage 48. These passages 46 and 48 are located so as to be immediately above small depressions 50 in the board 22. Except where the depressions 50 are located the base 38 is attached directly to the board 22 so as to overlie the strips 28, 30 and 32 through the use of a small layer 52 of a conventional electrically non-conductive adhesive. Various functional equivalent techniques such as ultrasonic welding can also be used to secure the housing 26 in place on the board 22.

The depressions 50 intersect the strips 28, 30 and 32; they are used to hold small bodies 54 of a conventional electrically conductive polymer composition so as to electrically connect the strips 28, 30 and 32 to individual electrodes 56 located in each of the passages 46 and 48. Other equivalent manners of establishing electrical connection between these parts can, of course, be employed. These electrodes 56 can be press-fitted in place or can be secured in position through the use of a conventional adhesive (not shown). When they are secured in place the electrodes 56 in the passages 46 extend upwardly into the cavities 42 and 44 while the electrode 56 extending through the passage 48 extends so as to be exposed to the bottom 58 of an enlarged, flat, disc-like depression 60 in the upper surface 62 of the top 40. Because of the shape and configuration of this depression 60 it may be regarded as a container or receptacle.

A stepped hole 64 having an upwardly facing shoulder 66 is located in the top 40 so as to lead downwardly from the depression 60 into the cavity 42. Another hole 68 is located in the top 40 so as to lead downwardly from the depression 60 into the cavity 44. The hole 64 below the shoulder 66 and the hole 68 are both filled with identical porous, electrically non-conductive plugs 70. These plugs 70 may be considered as flow restricting members or membranes. They may be press-fitted into place or may be secured in position through the use of an appropriate conventional adhesive (not shown). Both of these plugs 70 and the cavities 42 and 44 beneath them are completely filled with an electrolyte composition 72 as indicated in the ensuing text. In addition a small, comparatively thin membrane or barrier 74 as later discussed in this document is secured in place in a similar manner in the hole 64 against the shoulder 66.

The composition of the membrane 74 is quite important in connection with the sensor or sensing device 20. When this device 20 is to be used in detecting a specific ion this membrane 74 should be "selective" relative to such ion. Similarly if the device 20 is to be used in detecting and measuring two or more closely related ions the membrane should be "selective" in connection with all of such ions. The term "selective" as used in this discussion means that the material in the membrane 74 should be of a character which is such that it can be used in accordance with conventional prior art electrochemical practice so as to detect the presence or absence of an ion or such related ions in a fluid and, if such an ion or such ions are present, so as to provide an indication of the amount of such ions present in the sample.

Similarly if the device 20 is to be used to detect the presence of a gas or related gases in a sample and, if such a gas or gases are present, to provide an indication of the extent of such presence the membrane 74 should be of a type recognized by the prior art as effective for such purpose. Because of the fact that suitable compositions for use with ions and gases are known and because of the fact that the present invention does not pertain to the use of any specific membrane or barrier material it is not considered necessary or desirable to further discuss suitable membranes 74.

For the same reason it is not considered necessary to encumber this specification with a detailed discussion of suitable electrolytes or electrolyte compositions for use as an electrolyte composition 72 as indicated in the preceding. Although with the broad scope of the present invention it is possible that a known type of composition 72 in one of the cavities 42 and 44 could be different from a known type of composition 72 in the other cavity 42 or 44 and that the plugs 70 used in connection with these cavities 42 and 44 could be filled with a different, known type of electrolyte composition it is considered that anyone using such a mixture of different electrolyte compositions 72 would be bypassing one of the important aspects of the invention. This relates to what is termed herein as "precalibration" of the device 20.

With the present invention it is preferred that only one electrolyte composition 72 be used in both of the cavities 42 and 44 and in both of the plugs 70. It is further preferred that the same composition be used in forming a body 76 which fills the depression 60 and which lies against and covers the plug 70 which is exposed to the cavity 60 and the membrane 74. Although it is not necessary to use the body 76 with the device 20 as subsequently indicated it is preferred to employ it in connection with this device 20. Although it would be possible to achieve benefits in accordance with the invention if such a composition 72 was a liquid composition of a known or conventional character used in connection with ion and gas selective electrochemical measurements for a practical reason it is preferred to use a gelled electrolyte composition instead of such a liquid electrolyte composition.

This is because of the fact that a liquid is apt to flow out of any of the locations discussed during packaging, handling and use of a device 20 whereas a gelled electrolyte under the conditions to which a device 20 will be subjected will not normally flow from any location in which it is located. It is considered that gelled ion and gas selective electrolytes are well known. Hence, it is not considered necessary to discuss them in detail in this specification. Normally they will be prepared by adding a suitable gelling agent such a a polyacrylamide or other known polymer composition which will cross-link on gelling to a liquid electrolyte and then placing the electrolyte in a desired final location before the gelling agent causes a gel to form.

With the sensor or sensing device the cavities 42 and 44 and the plugs 70 can be filled concurrently by vacuum impregnation with the composition 72 before it has gelled prior to the membrane 74 being located in its final position. Then, after the membrane 74 has been located in place, by casting some of the same composition 72 in the depression 60 so as to create the body 76. It will be recognized that there can be considerable variation in both the composition of the electrolyte used as the composition 72 and in forming the body 76. In effect the latter really should also be referred to as an electrolyte composition because of its function.

In accordance with the invention the electrolyte composition 72 and the body 76 should be of the same or substantially the same electrochemical characteristics. Obviously when the composition and the body 76 all have exactly the same ingredients this is the case. When the composition 72 and the body 76 are the same there will be no ion movement within or between the composition and the body 76 since there is no ion concentration differential present. Substantially the identical considerations are involved in connection with electrolytes for use in gas analysis. As a consequence a device 20 as described herein can be precalibrated prior to its being delivered to or used by an ultimate user. As subsequently discussed such a user need only to remove the body 76 and to substitute a sample or specimen (not shown) in making a desired determination.

As supplied to a user the device preferably includes a small impervious, polymer protective cover or cap 78 which fits tightly against the top 40 so as to close or seal off the depression 60 from ambient influences. Although this cap 78 can be held in place merely by fitting tightly against the housing 26 it can also be held in place by a conventional tacky adhesive (not shown) or by a small, easily broken weld or seal (not shown). If desired the cap 78 and the body 76 can be secured together by a mechanical interlock (not shown) or by a common adhesive (not shown) so that when the cap 78 is removed the body 76 will also automatically be lifted away from the housing 26.

When the device 20 as supplied to a user is to be employed it is necessary to perform a series of minor steps in order to prepare it for use. The sequence of these steps can be varied as desired. The device 20 may initially be "plugged" into female socket of an electronic apparatus as discussed in the preceding. Next the cover or cap may be removed from the housing 26 by simply being lifted or torn off of the housing 26. Following this if the body 76 was not lifted out of the depression 60 when the cap 78 was removed it can be removed from the depression using any convenient manipulative tool such as tweezers (not shown). At this point the device or sensor 20 is ready to be used.

As it is used the depression 60 will be filled with a liquid sample or specimen to be examined. Because of the location of the depression 60 it will be normally rather easy to fill it with a small quantity of such a sample of specimen. This filling of the depression 60 will place the liquid to be analyzed in direct contact with the membrane 74, one of the plugs 70 and the electrode 56. The plug 70 associated with the cavity 44 will tend to isolate such liquid from the electrolyte composition 72 within the cavity 44. Although to a degree the plug 70 associated with the other cavity 42 does this it primarily serves to reinforce or support the membrane 74 while concurrently isolating such liquid.

As a consequence of this the membrane 74 can be comparatively thin and/or weak without there being significant danger of it being cracked or otherwise damaged. This is important for economic reasons since it makes it possible to minimize the material in the membrane 70. It can also be desirable for other reasons. When the depression 60 is filled the liquid filling it in effect "bridges" the cavities 42 and 44 in a manner which is related to the manner in which a conventional bridge used in prior electrochemical measurements extends between and connects two separate half cells.

In the device 20 in effect the housing 26 acts as a common housing for two such half cells designated by the numerals 80 and 82. The first of these half cells, the half cell 80 includes the portions of the housing 26 surrounding the cavity 42, the electrode 56 extending into this cavity 42, the electrolyte composition 72 within it, the plug 70 associated with it and the membrane 74. This first half cell 80 may be referred to as a "sensing" cell because the membrane 74 makes it possible to use this sensing half cell 80 to provide a signal indicative of the presence or absence of an ion or ions or a gas or gases in the specimen and if appropriate an indication of the quantity of the same present.

The second half cells 82 includes the portions of the housing 26 surrounding the cavity 44, the electrode 56 extending into this cavity 44, the electrolyte composition 72 within this cavity 44 and the plug 70 associated with it. This second half cell 82 can be referred to as a "reference" cell because it is used to provide a reference reading or signal in accordance with conventional practice.

In order to obtain such signals or readings from these two half cells 80 and 82 the electronic apparatus into which the device or sensor 20 has been plugged can now be operated in a conventional manner. During such operation the electrode 56 extending into the depression 60 will be in contact with the liquid being analyzed and may be used as a ground in making accurate measurements in accordance with a technique not forming part of this invention. Inasmuch as the manner in which such operation of an appropriate electronic apparatus is known it is not described in detail in this document.

After a reading is obtained the device or sensor 20 can be unplugged and discarded. In some cases such as in some non-medical uses it may be desirable to attempt to clean out the device or sensor 20 so that it can be used again. To do this it is only necessary to dump out the liquid in the depression 60 and then rinse out the depression 60 before the sensor 20 is used again. Such subsequent use should be soon enough after the prior use so that the electrolyte composition 72 will not significantly dry out.

Figure 9:
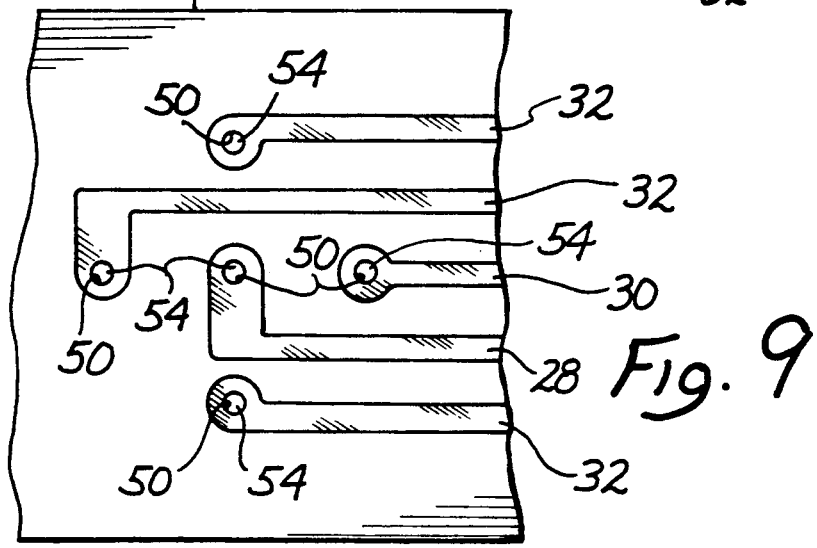
FIG. 9 is a partial cross-sectional view taken at line 9—9 of FIG. 7 which approximately corresponds to FIG. 4.
Figure 6:
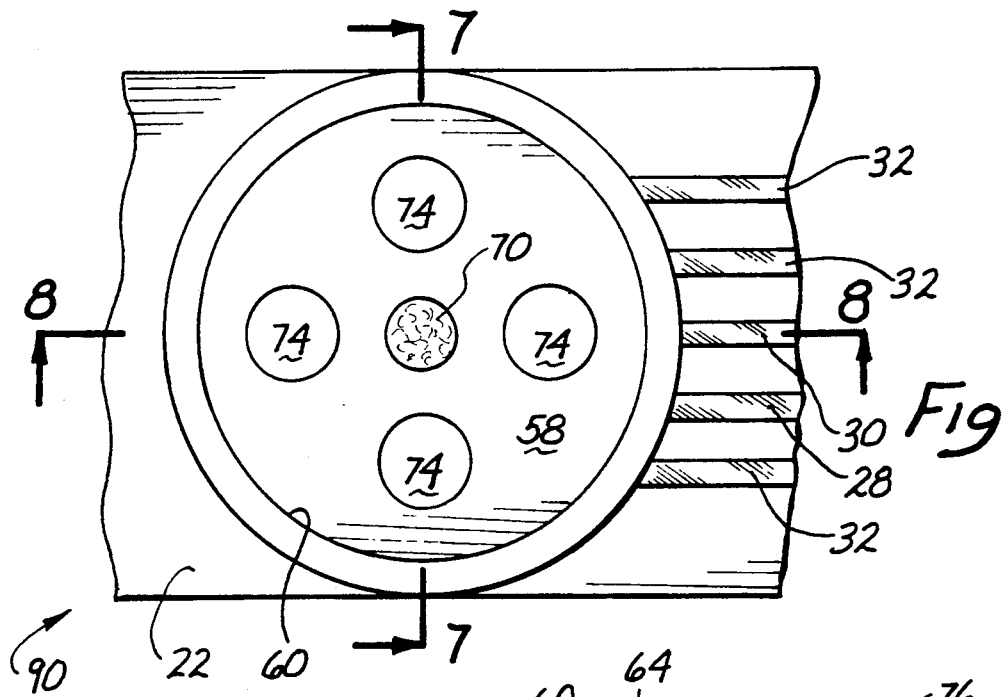
FIG. 6 is a partial view similar to FIG. 5 of a modified embodiment of a sensing device or sensor of this invention which is presently preferred for use in making a series of different, separate analyses substantially concurrently with a cover in place on the device and with a removable body of an electrolyte in place within the device.
Figure 7:
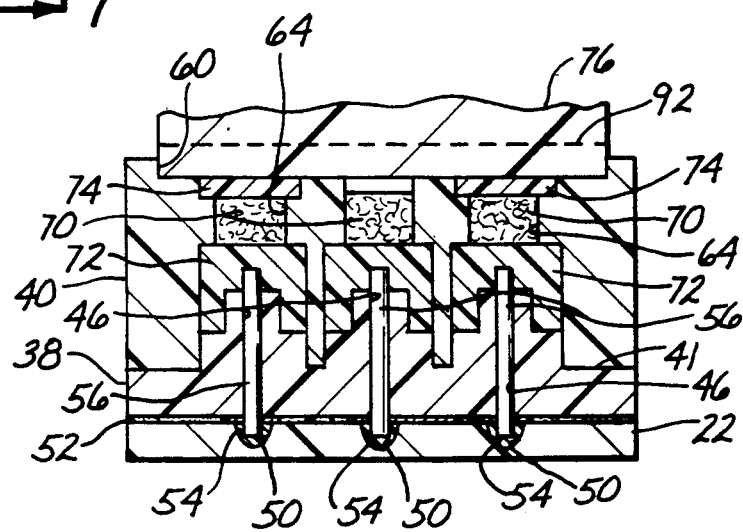
FIG. 7 is a cross-sectional view taken at line 7—7 of FIG. 6 which approximately corresponds to FIG. 3.
Figure 8:
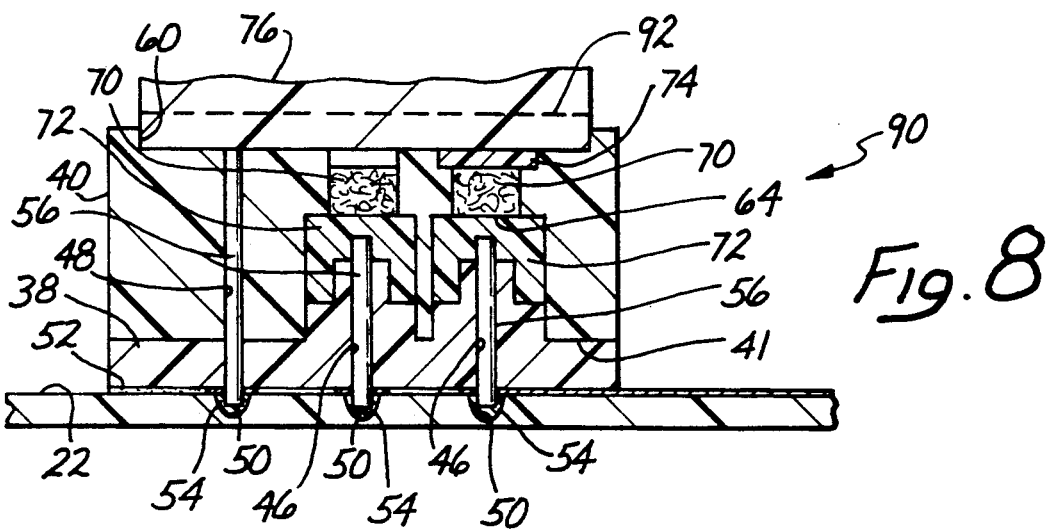
FIG. 8 is a cross-sectional view taken at line 8—8 of FIG. 6 which approximately corresponds to FIG. 3.

In FIGS. 6 to 9 of the drawings there is shown a modified disposable electrochemical sensing device or sensor 90 in accordance with the invention which is quite closely related to the sensor 20 described in the preceding. In the interest of brevity those parts of the sensor 90 which are the same or substantially the same as corresponding parts of the sensor 20 are designated in this document by the same numerals as have been employed to designate such corresponding parts in the preceding and in the drawing. Since it does not appear necessary to an understanding of the sensor 90 the cap 78 described in connection with the sensor 20 is not illustrated in FIGS. 6 to 9. It is to be understood that this cap 78 is normally suppled with the sensor 90.

The sensor 90 differs from the device or sensor 20 in that the sensor 20 is constructed so as to include only two half cells 80 and 92 as previously discussed whereas the sensor 90 includes 1 half cell 82 and 3 half cells 80. Of course the housing 26 has to be modified as shown in the drawings so as to create these half cells 80 and 82. In the device 90 the half cells 80 and the electrode 56 previously described as being used for grounding purposes are arranged in a circular pattern around the half cell 82. The device 90 uses a strip 30 for each of the half cells 82. It also uses an enlarged depression 60 which is large enough so as to place a relatively small quality of a sample or specimen in liquid contact with all of the cells 80 and 82 and with the electrode 56 discussed earlier in this paragraph.

In the sensor 90 the various sensing half cells 82 can be constructed in either of two different manners. This is not illustrated in the drawings because the differences in these two constructions pertains to the electrolyte compositions 72 used in the various half cells 82 and the nature of the membranes 74 used in these half cells 82. In both manners of construction the depression serves as a bridge means connecting all of the half cells 82 in the sensor 90.

In the first of these two different manners the electrolyte compositions 72 in all of the sensing half cells 82 and, if as is preferable, the body 76 is used, in the body 76 have substantially the same electrochemical characteristics. Preferably the electrolyte compositions and the body 76 should be identical so as to make sure that their electrochemical characteristics are the same. If desired one of the half cells 82 can be set up or constructed in a conventional manner so as to be capable of being used to detect pH.

In this first manner of constructing the sensor 90 the membranes 74 used in the various half cells 82 are different from one another but are all related so as to be selective so as to be capable of being used to make a series of separate analyses for related items such as several alkaline earth ions (such as calcium and magnesium) and pH. As a further example of this such a series of membranes 74 could also be selective with respect to sodium, potassium and chloride ions. The use of any sensor 90 constructed in this manner is essentially the same as the use of the sensor 20 described in the preceding.

In the second of these manner of constructing the sensor 90 the membrane 74 in each of the half cells 82 is preferably different from the membrane 74 in each of the other half cells 82. Further, the electrolyte compositions 72 used with these half cells 82 are also preferably different from one another and are of such a character as to be effective for use in making electrochemical measurements with the membranes 74 with which they are associated. Since such relationships of selective membranes and electrolyte compositions for use with such membranes is well known it is not considered necessary to discuss it in detail.

As a result of the differences in the electrolyte compositions 72 in the cells 82 in the device 90 as described in the preceding it is impossible to use a single body 76 which is of the same composition as all of the these compositions 72. As a consequence of this the body 76 is replaced in the device or sensor 20 with a small impervious disc 92 indicated by dotted lines which is held in place within the cavity 60 by a pressure sensitive adhesive (not shown) so that a tab 92 on this disc 92 can be used to easily remove the disk 92 in order to permit a specimen or sample to be located within the depression 60.

After such a sample is in place a series of measurements of analyses may be made as previously discussed using the half cell 80 in all of the measurements or determinations and with a different half cell 82 in each. In making such determinations it normally will be necessary to calibrate the sensor 20 in connection with each separate measurement. In all other respects the use of the sensor or device 90 is the same as the use of the sensor or device 20.

I claim:

1. An electrochemical device which has two half cell means,
    each of said half cell means including a housing means having an interior cavity and an entrance into said cavity, electrode means exposed to the interior of said cavity and extending to the exterior of the half cell means,
    bridge means in communication with said entrances to both said half cell means and
    in which the improvement comprises:
    said bridge means is shaped as a receptacle having an upwardly opening open top, said bridge means formed as an integral part of said housing means,
    cover means for forming a reversible seal, said cover means located on said bridge means to seal said open top of bridge means receptacle,
    barrier means for forming a barrier permeable to only select ions, said barrier means positioned in association with the entrance of one of said half cells means between said one of said half cell means and said bridge means receptacle,
    a unified body of non-fluid, immobilized, cross-linked gel having a homogenous electrolyte containing therein, a portion of said gel permanently and fixedly located in said half cell interior cavities in contact with said electrodes in said cavities and further in contact with said barrier means, the remaining portion of said gel located in said bridge means receptacle and sealed in said receptacle by said cover means.

2. An electrochemical device as claimed in claim 1 further including:
    each of said half cell means including a porous restriction means for enclosing the entrance to said half cell means, said porous restriction means positioned in operative association with the entrance of said half cell between said half cell means and said bridge means,
    said barrier means supported on one of said porous restriction means; and
    said part of said portion of said gel located in said half cell interior located in the pores of said porous restriction means.

3. A device for use in making electrochemical measurements which includes:
    an electrically non-conductive self supporting, elongated bottom board having a tab-like portion at a first end thereof for use in manipulating said device and a second end capable of being inserted into an electrical socket,
    an electrically non-conductive housing rigidly mounted on said bottom board intermediate said first and second ends of said board and extending upwardly from said bottom board,
    said housing being shaped so as to include a depression capable of serving as a receptacle at the top thereof, said housing further including two separate internal cavities formed therein generally beneath said depression and holes leading from the bottom of said depression into the interior of each of said cavities,
    an electrode extending from a position adjacent to said board into the interior of each of said cavities,
    an electric conductor corresponding to each of said electrodes located on said board so as to extend from said second end of said board to a position underneath said housing, said conductor being located so as to be capable of being electrically connected to a circuit using a socket, each of said conductors being electrically connected to one of said electrodes,
    a selective membrane means extending across one of said holes,
    porous flow restricting means located in both of said holes, said selective membrane means being located on one of said flow restricting means,
    a unified body of non-fluid, immobilized, cross-linked gel having a homogenous electrolyte containing therein, a portion of said gel permanently and fixedly located within the pores of said flow restricting means, a further portion of said gel permanently and fixedly located in each of said cavities and being in contract with said electrodes in said cavities and said flow restricting means.

4. A device as claimed in claim 3 including:
    an additional portion of said gel containing said electrolyte therein being located within said depression in contact with said selective membrane means in said one of said holes and in further contact with said further portion of said gel containing said electrolyte therein through the other of said holes, said additional portion of said gel containing said electrolyte therein for use in calibrating said device, said additional portion of said gel containing said electrolyte therein being capable of being removed from said depression prior to said device being used by an ultimate user.

5. A device as claim 4 further including:
    cover means enclosing said open top and said additional portion of said gel containing said electrolyte therein.

6. A device as claimed in claim 3 wherein:
    said housing and said depression are shaped so that an additional portion of said gel containing said electrolyte therein can be located within said depression in contact with said selective membrane in said one of said holes and in further contact with said further gel containing said electrolyte therein in the other said holes for use in calibrating said device and can be removed from said depression prior to said device being used by an ultimate user.

7. A device as claimed in claim 6 including:
    a third electrode adapted to be used as a ground held by said housing so as to extend from the bottom thereof to the interior of said depression, a third electrical conductor located on said board adjacent to said other conductors and being electrically connected to said third conductor.

8. A device as claimed in claim 3 wherein:

said housing is shaped so as to include additional cavities in excess of said two of said cavities and includes a separate electrode and electric conductor in association with each of said cavities, and including, a flow restricting means located in each of said holes of said additional cavities, a selective membrane means extending across each of said holes of said additional cavities, said membranes all differing electrochemically from each other, and further portions of said gel containing said electrolyte located within and filling each of said additional cavities.

9. A device as claimed in claim 8 wherein:

said cavities are arranged so that the cavity which contains one of said holes is centrally located with respect to the other of said cavities.

10. A device as claimed in claim 8 including a further electrode adapted to be used as a ground held by said housing so as to extend from the bottom thereof to the interior of said depression, a further electrical conductor located on said board adjacent to said other conductors and other electrically conductive means connecting said further electrode with said further conductor.

* * * * *